United States Patent

Tomiuchi et al.

[11] Patent Number: 5,968,697
[45] Date of Patent: Oct. 19, 1999

[54] ELECTROPHOTOGRAPHIC PHOTOCONDUCTOR

[75] Inventors: Toshimasa Tomiuchi; Masahiko Kasahara, both of Nagano, Japan

[73] Assignee: Fuji Electric Co., Ltd., Kawasaki, Japan

[21] Appl. No.: 09/030,744

[22] Filed: Feb. 25, 1998

[30] Foreign Application Priority Data

Feb. 27, 1997 [JP] Japan .................................. 9-043171

[51] Int. Cl.$^6$ ................................................. G03G 5/047
[52] U.S. Cl. ............................................... 430/83; 430/58
[58] Field of Search ............................ 430/58, 59, 83

[56] References Cited

U.S. PATENT DOCUMENTS 5,702,855  12/1997  Ikegami et al. ......................... 430/83
5,846,680  12/1998  Adachi et al. ............................. 430/83

*Primary Examiner*—John Goodrow
*Attorney, Agent, or Firm*—Baker & Botts, L.L.P.

[57] ABSTRACT

An electrophotographic photoconductor comprises:
(a) a conductive substrate; and
(b) a photoconductive film on said conductive substrate, with the photoconductive film comprising at least one charge generation agent, at least one charge transport agent, and at least one furan derivative or thiophene derivative, the furan or thiophene derivative having the general formula:

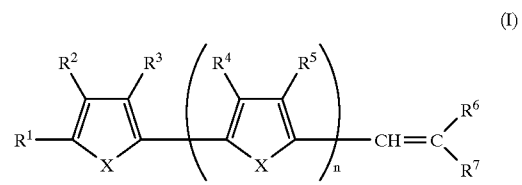

(I)

or

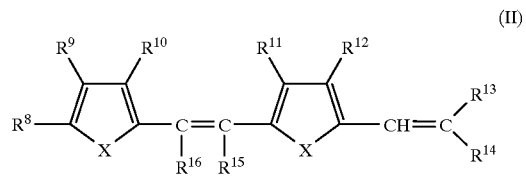

(II)

8 Claims, 1 Drawing Sheet

ELECTROPHOTOGRAPHIC PHOTOCONDUCTOR

BACKGROUND OF THE INVENTION

This invention relates to an improved photoconductive film of electrophotographic photoconductors used for printers and copying machines which employ electrophotographic processes. More specifically, this invention relates to constituent materials of the photoconductive film.

Conventional photosensitive materials of the electrophotographic photoconductor (hereinafter simply referred to as a "photoconductor" used for the printers, facsimile machines, digital copying machines and analog copying machines) employed in electrophotographic processes include inorganic photoconductive materials such as selenium, selenium alloys deposited by vacuum deposition zinc oxide and cadmium sulfide dispersed into resin binder, organic photoconductive materials such as poly-N-vinylcarbazole, poly(vinyl anthracene), phthalocyanine compounds and bisazo compounds dispersed into resin binder or deposited by vacuum deposition.

It is required that the photoconductor retain surface charges in the dark, generate electric charges in response to the received light, and transport electric charges in response to the received light. The photoconductor may be classified into either the mono-layered-type, that exhibits the above described functions using one single photoconductive film, or the so-called laminate-type, that consists of one layer mainly for charge generation and another layer for charge retention in the dark and for charge transport in response to the received light. The electrophotographic techniques for image formation using the aforementioned types of photoconductors include the Carlson's process. The Carlson's process for image formation includes charging of the photoconductor by corona discharge in the dark, formation of electrostatic latent images of the letters and figures in a manuscript on the charged surface of the photoconductor, development of the electrostatic latent images with toner, and fixing of the developed toner images on a paper or other such carriers. The photoconductor is used again after charge removal, residual toner removal and optical charge removal.

Various image formation steps are employed in the Carlson's process. The corotron method or the scorotron method that uses metal wire and the contact charging method that uses the charging brush or charging roller are used for charging the photoconductor. The two-component development method, nonmagnetic-single-component development method, and magnetic-single-component development method may be used in the development step.

Recently, organic photoconductors have been developed by virtue of the flexibility, thermal stability and ease of film formation thereof. U.S. Pat. No. 3,484,237 discloses a photoconductor that includes poly-N-vinyl carbazole and 2,4,7-trinitrofluorenone. Japanese Unexamined Laid Open Patent Application No. S47-37543 discloses a photoconductor that includes an organic pigment as the main component thereof. Japanese Unexamined Laid Open Patent Application No. S47-10785 discloses a photoconductor that includes an eutectic complex consisting of a dye and resin as the main component thereof. At present, the function-separation-type organic photoconductors, which include a charge generation layer and a charge transport layer, are mainly used. The charge generation layer comprises metal-free phthalocyanine, metal phthalocyanine such as titanyl phthalocyanine or azo compound and a resin binder. The charge transport layer contains a hydrazone compound, styryl compound, diamine compound or butadiene compound and a resin binder.

Although the organic photoconductive materials have many advantages over inorganic photoconductive materials, the conventional organic photoconductive materials do not exhibit all the properties required of an electrophotographic photoconductor. It is desired to obtain a highly sensitive photoconductor that exhibits little change in the properties thereof after the photoconductor is continuously used in the electrophotographic apparatus for a long time. The aforementioned capability is especially important because of the customer's increasing demand for photoconductors which are durable enough to endure long continuous use in various electrophotographic devices using the foregoing imaging processes. The photosensitivity of the conventional laminate-type photoconductors are insufficient. Practical long use of the conventional laminate-type photoconductors causes charge potential lowering, residual potential rise, sensitivity lowering, and such problems have yet to be solved. Thus, there is a need for a technology that facilitates realizing all the favorable properties for the electrophotographic photoconductor.

In view of the foregoing, it is an object of the invention to provide an electrophotographic photoconductor that is stable enough to endure repeated continuous use for an extended time in practical electrophotographic devices. It is another object of the invention to provide an electrophotographic photoconductor that is fully adaptable to various electrophotographic devices which employ the corotron method or the scorotron method that uses metal wire for charging, which employ the contact charging method that uses the charging brush or charging roller for charging, which employ the two-components-development method, which employ the nonmagnetic-single-component development method and which employ the magnetic-single-component development method.

SUMMARY OF THE INVENTION

It has been found that the foregoing problems are solved by an electrophotographic photoconductor that contains a photoconductive film having at least one compound selected from specific furan derivatives and thiophene derivatives.

According to one embodiment of the invention, there is provided an electrophotographic photoconductor that includes a conductive substrate, a photoconductive film on the conductive substrate, with the photoconductive film including at least one furan derivative or thiophene derivative described by the general formula:

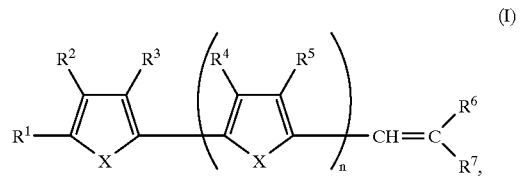

(I)

where $R^1$ is a hydrogen atom, halogen atom, substituted or non-substituted alkyl group, alkoxy group, cyano group, substituted or non-substituted heterocyclic group, or substituted or non-substituted aromatic group; $R^2$ is a hydrogen atom, halogen atom, substituted or non-substituted alkyl group, alkoxy group, cyano group, substituted or non-substituted heterocyclic group, or substituted or non-substituted aromatic group; $R^3$ is a hydrogen atom, halogen atom, substituted or non-substituted alkyl group, alkoxy group, cyano group, substituted or non-substituted heterocyclic group, or substituted or non-substituted aromatic group; $R^4$ is a hydrogen atom, halogen atom, substituted or non-substituted alkyl group, alkoxy group, cyano group, substituted or non-substituted heterocyclic group, or substituted or non-substituted aromatic group; $R^5$ is a hydrogen atom, halogen atom, substituted or non-substituted alkyl group, alkoxy group, cyano group, substituted or non-substituted heterocyclic group, or substituted or non-substituted aromatic group; $R^6$ is a cyano group, or alkoxycarbonyl group; $R^7$ is a cyano group, or alkoxycarbonyl group; X is an oxygen atom or sulfur atom; and n is an integer having a value of 0 or 1.

According to another embodiment of the invention, there is provided an electrophotographic photoconductor that includes a conductive substrate, a photoconductive film on the conductive substrate with the photoconductive film including at least one charge transport agent which is a furan derivative or thiophene derivative described by the general formula:

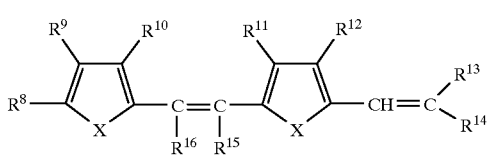

(II)

where $R^8$ is a hydrogen atom, halogen atom, substituted or non-substituted alkyl group, alkoxy group, cyano group, substituted or non-substituted heterocyclic group, or substituted or non-substituted aromatic group; $R^9$ is a hydrogen atom, halogen atom, substituted or non-substituted alkyl group, alkoxy group, cyano group, substituted or non-substituted heterocyclic group, or substituted or non-substituted aromatic group; $R^{10}$ is a hydrogen atom, halogen atom, substituted or non-substituted alkyl group, alkoxy group, cyano group, or substituted or non-substituted heterocyclic group, or substituted or non-substituted aromatic group; $R^{11}$ is a hydrogen atom, halogen atom, substituted or non-substituted alkyl group, alkoxy group, cyano group, substituted or non-substituted heterocyclic group, or substituted or non-substituted aromatic group; $R^{12}$ is a hydrogen atom, halogen atom, substituted or non-substituted alkyl group, alkoxy group, cyano group, substituted or non-substituted heterocyclic group, or substituted or non-substituted aromatic group; $R^{15}$ is a hydrogen atom, halogen atom, substituted or non-substituted alkyl group, alkoxy group, cyano group, substituted or non-substituted heterocyclic group, or substituted or non-substituted aromatic group; $R^{16}$ is a hydrogen atom, halogen atom, substituted or non-substituted alkyl group, alkoxy group, cyano group, substituted or non-substituted heterocyclic group, or substituted or non-substituted aromatic group; $R^{13}$ is a cyano group, or alkoxycarbonyl group; $R^{14}$ is a cyano group, or alkoxycarbonyl group; and X an oxygen atom or sulfur atom.

The alkyl group and the alkoxy group for the groups $R^1$ through $R^5$ in the general formula (I) preferably contain from one to eight carbon atoms.

The alkyl group and the alkoxy group for the groups $R^8$ through $R^{12}$, $R^{15}$ and $R^{16}$ in the general formula (II) preferably contain from one to eight carbon atoms.

DESCRIPTION OF THE DRAWINGS

The invention will be more readily understood from the description of a preferred embodiment that follows and from the diagrammatic figures in the drawings.

In the drawings.

DETAILED DESCRIPTION OF THE INVENTION

Figure 1:
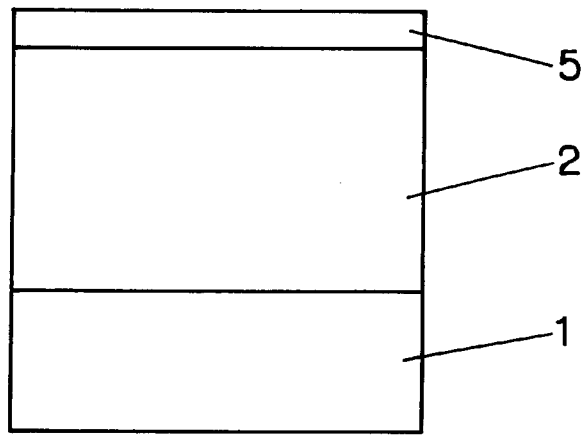
FIG. 1 shows a cross section of an electrophotographic photoconductor including a monolayered photoconductive film according to the present invention.

The furan derivatives and the thiophene derivatives described by the general formulas (I) and (II) have not previously been used in electrophotographic photoconductors. However, it has now been discovered that photoconductors employing the furan derivatives and the thiophene derivatives described by the general formulas (I) and (II) exhibit high sensitivity, and that the electrical potential characteristics and sensitivity characteristics of the photoconductor are not deteriorated by their long term use in various electrophotographic devices. Thus, excellent electrophotographic properties are realized by adding the furan derivatives or the thiophene derivatives as described by the general formula (I) or (II) to the photoconductive film.

While not wishing to be bound by any one theory it is believed that the deterioration of electrophotographic photoconductors (e.g. lowering of charge potential, increase in residual potential, and decrease of sensitivity after repeated use) may be attributed to the formation of carrier trap centers in the photoconductive film due to repeated stresses incurred in the electrophotographic process, such as charging, light exposure, and development. Accordingly, it is believed that the use of an electron-attracting compound or compounds such as the furan and thiophene compounds of general formulas (I) and (II) suppress carrier trap formation. The photoconductive films of this invention containing the furan or thiophene compounds of general formulas (I) and (II) have been found to exhibit excellent electrical potential characteristics and high sensitivity after long term use in various electrophotographic processes.

Examples of the thiophene derivatives and the furan derivatives described by the general formula (I) are described as follows:

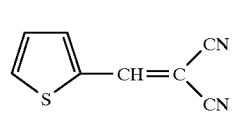

I-1

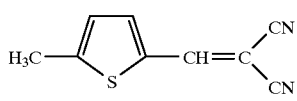

I-2

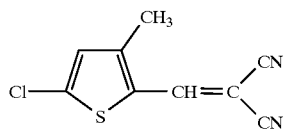

I-3

-continued
I-4
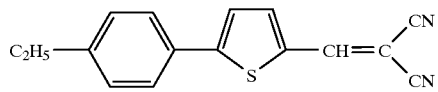
I-5
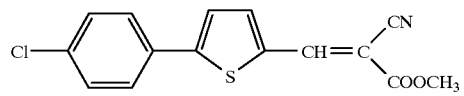
I-6
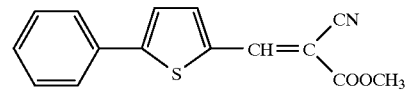
I-7
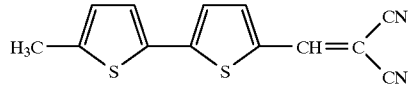
I-8
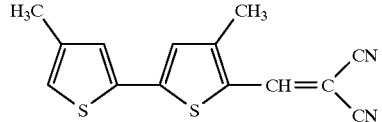
I-9
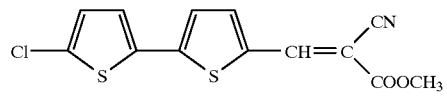
I-10
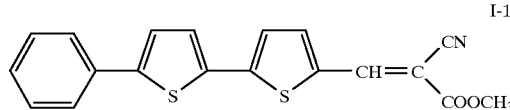
I-11
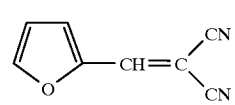
I-12
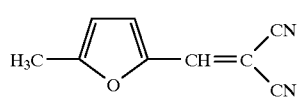
-continued
I-13
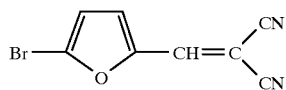
I-14
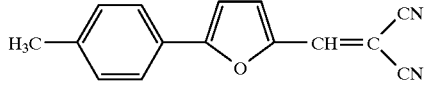
I-15
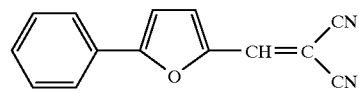
I-16
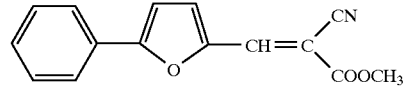
I-17
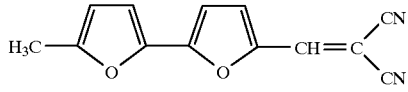
I-18
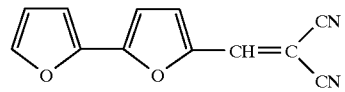
I-19
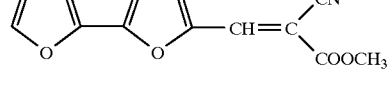
I-20
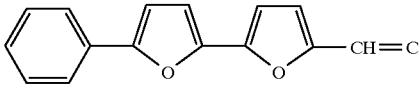
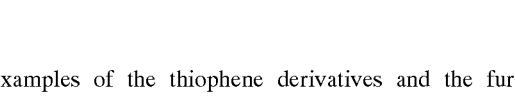
Examples of the thiophene derivatives and the furan derivatives described by the general formula (II) are described as follows:
II-1
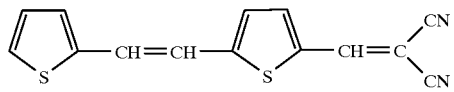
II-2
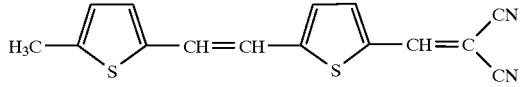
II-3
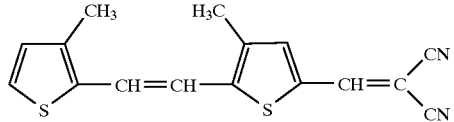

II-4
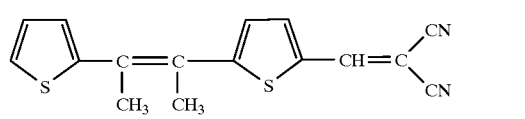
II-5
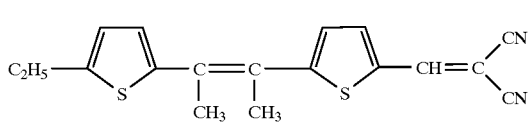
II-6
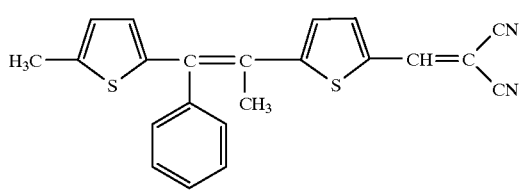
II-7
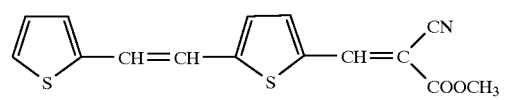
II-8
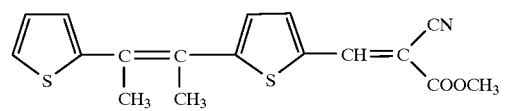
II-9
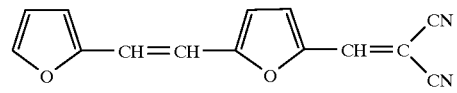
II-10
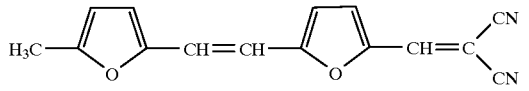
II-11
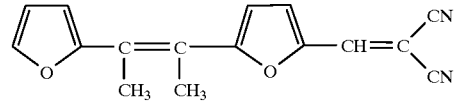
II-12
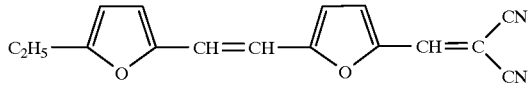
II-13
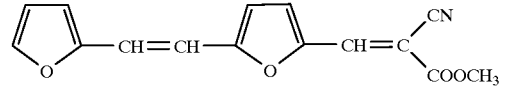
II-14
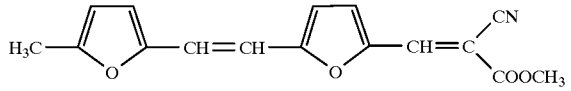
II-15
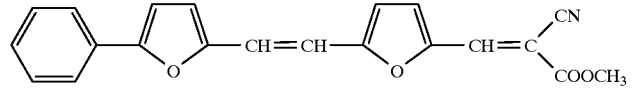

II-16
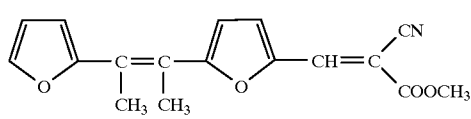
Examples of the charge generation agent used in the present invention include phthalocyanine compounds (III-1) through (III-6), and azo compounds including the derivatives thereof (III-7) through (III-24), as follows:
(III-1)
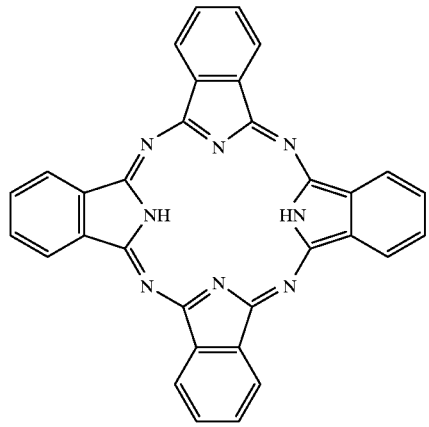
(III-2)
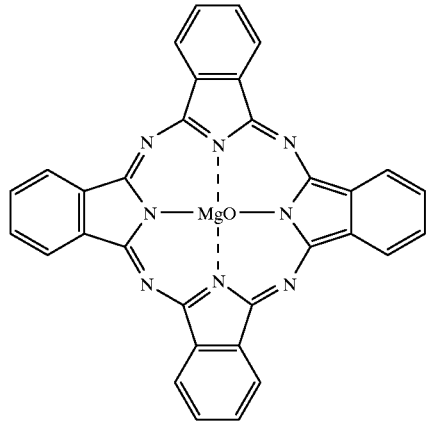
(III-3)
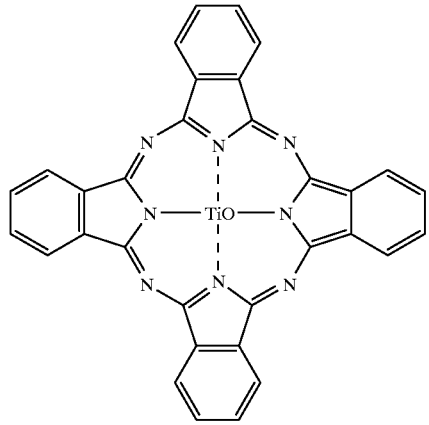

(III-4)
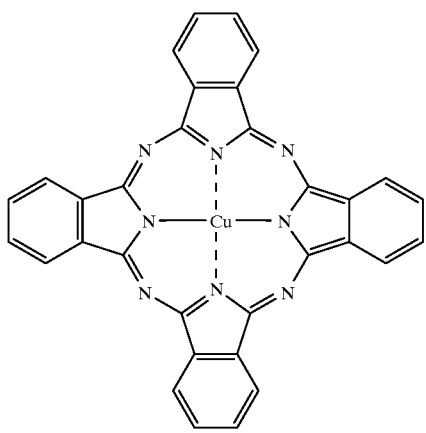
(III-5)
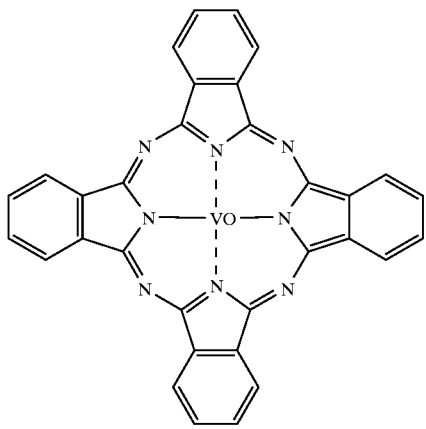
(III-6)
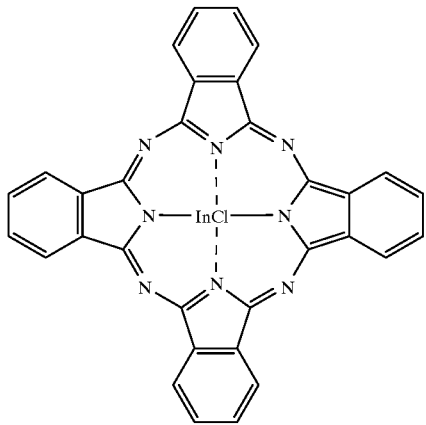
(III-7)
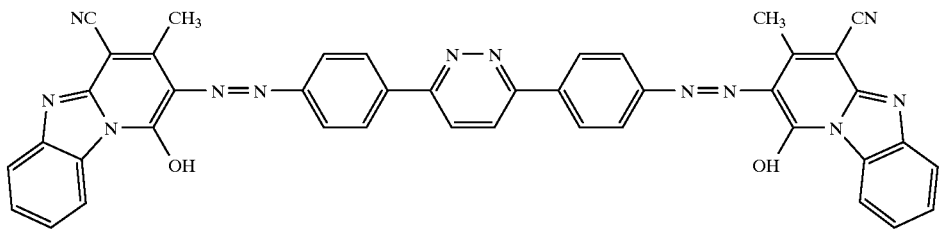

-continued
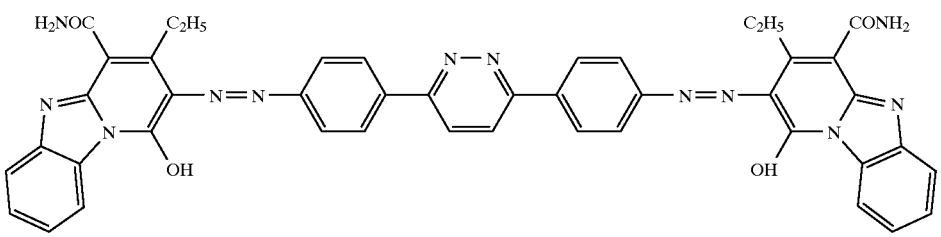
(III-8)
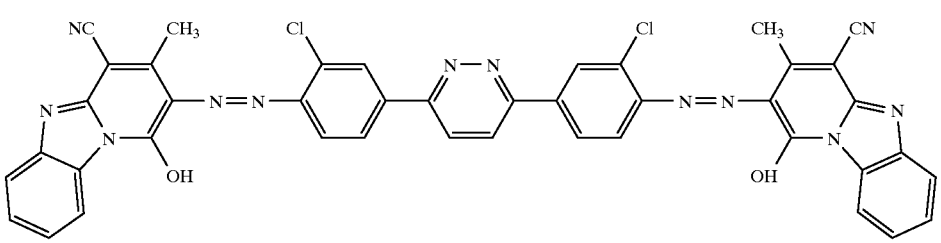
(III-9)
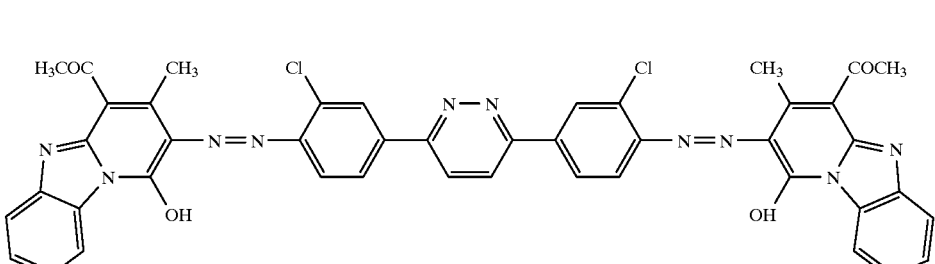
(III-10)
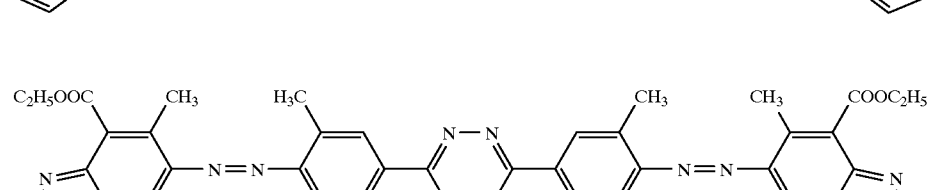
(III-11)
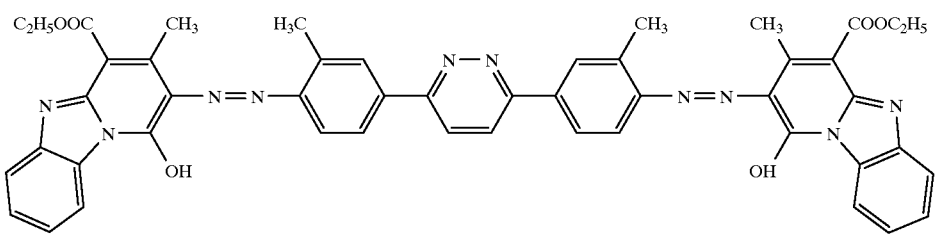
(III-12)
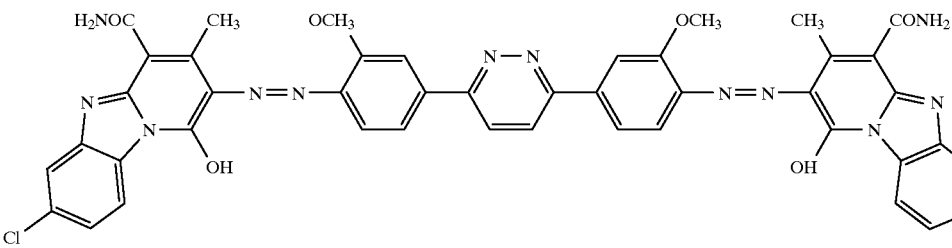
(III-13)
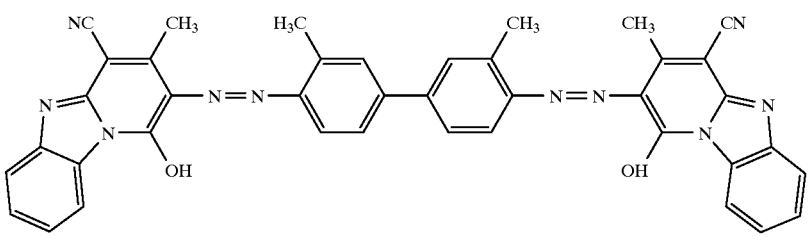

-continued
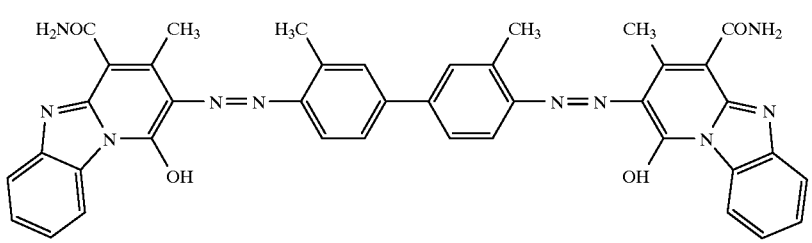
(III-14)
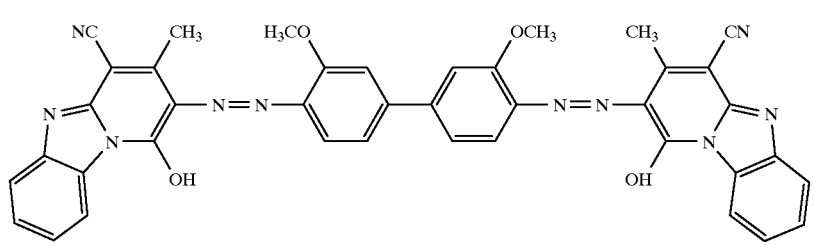
(III-15)
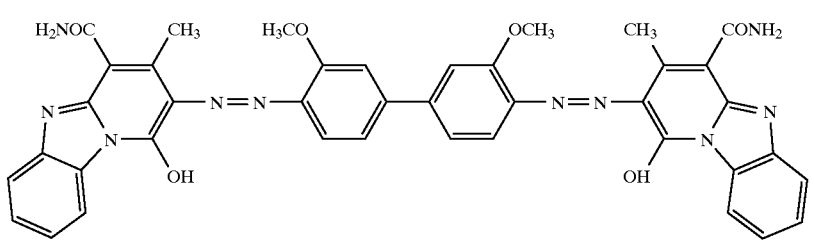
(III-16)
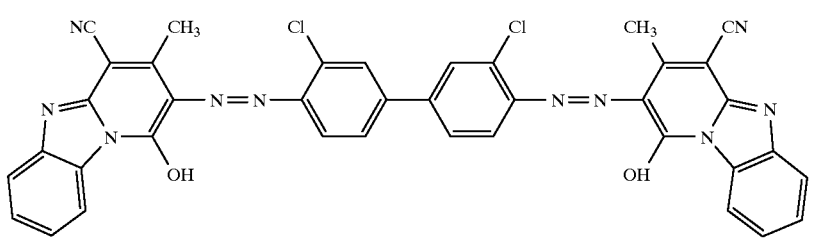
(III-17)
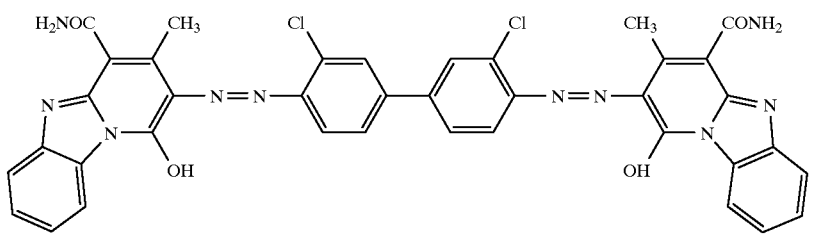
(III-18)
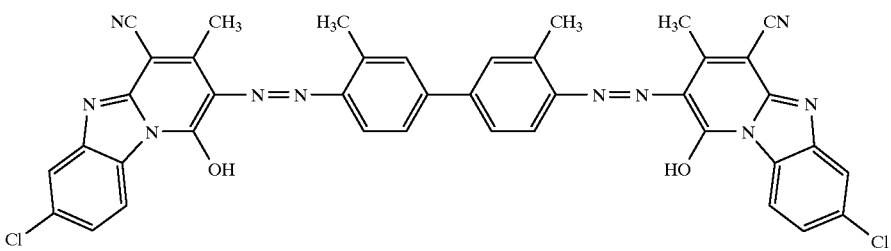
(III-19)

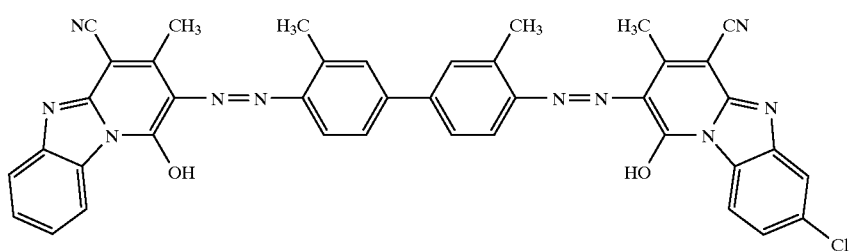
(III-20)
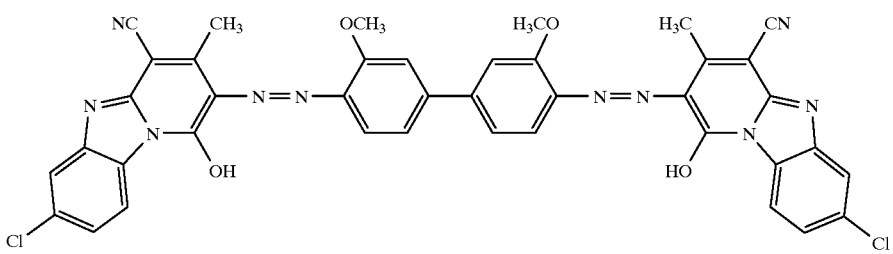
(III-21)
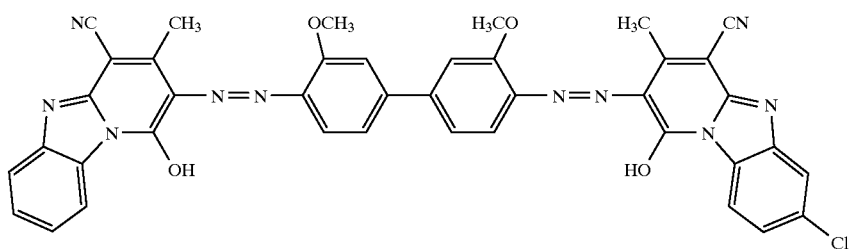
(III-22)
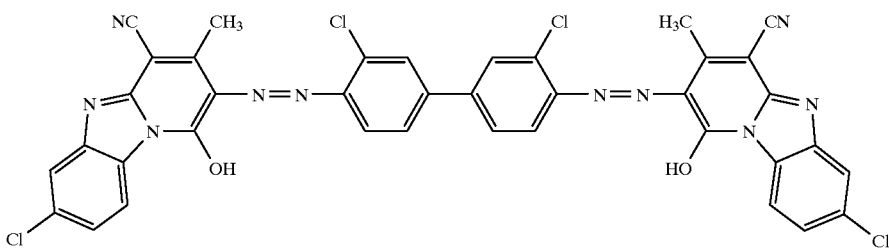
(III-23)
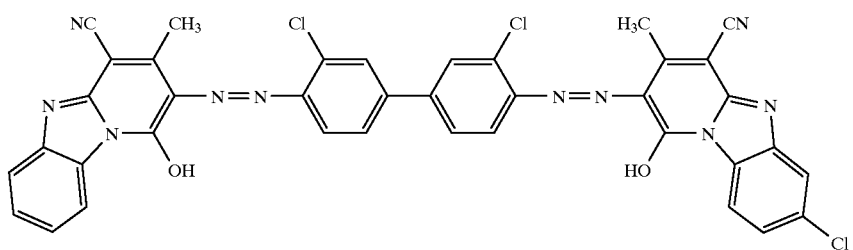
(III-24)

Various compounds (IV-1) through (IV-12) which may be used in combination with the furan derivatives and the thiophene derivatives described by the general formulas (I) and (II) have the following formulas:
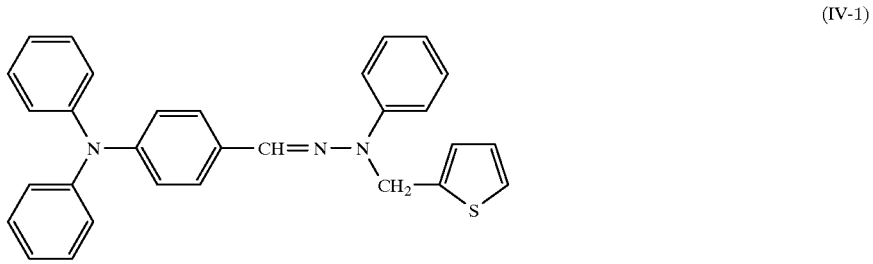
(IV-1)
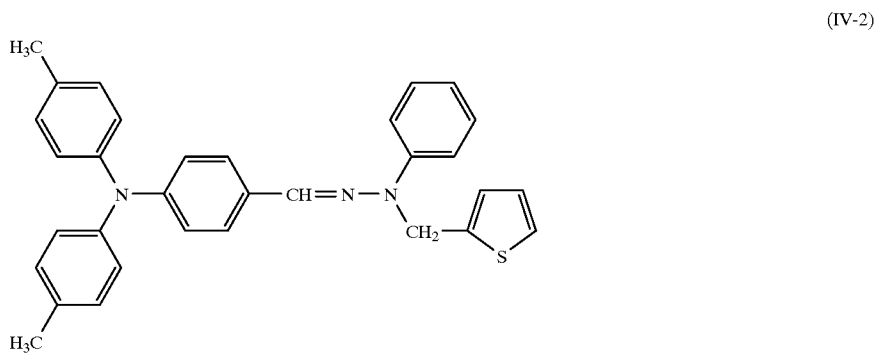
(IV-2)
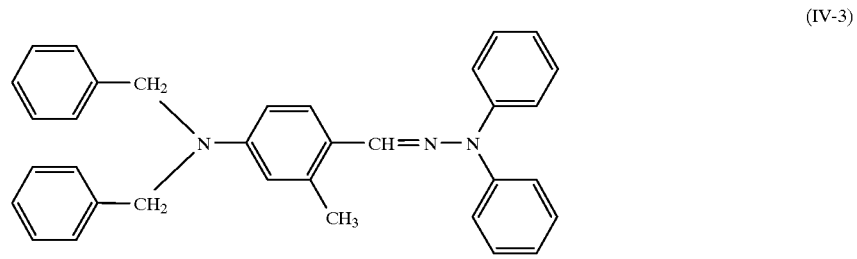
(IV-3)
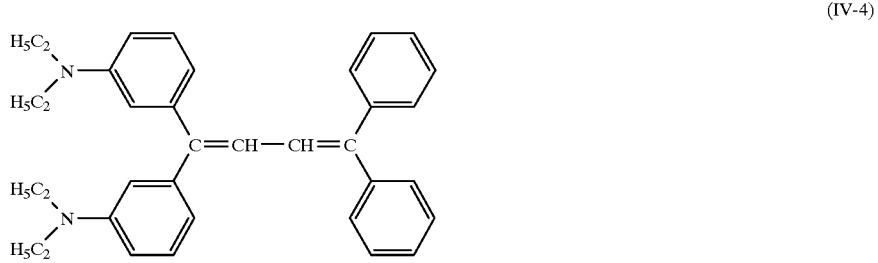
(IV-4)
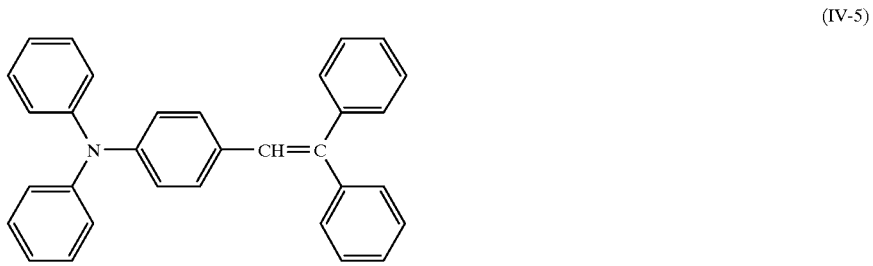
(IV-5)

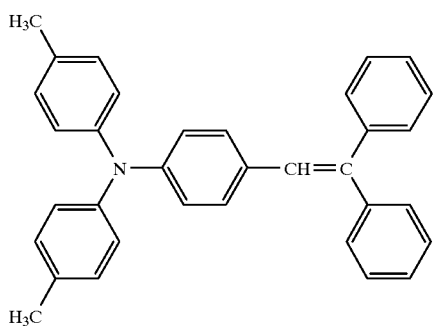
(IV-6)
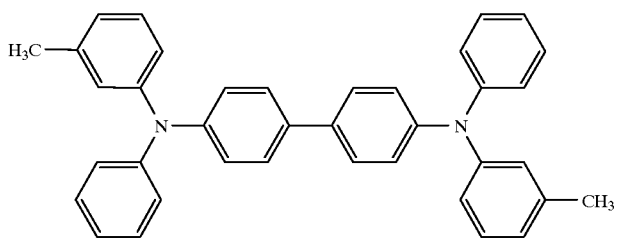
(IV-7)
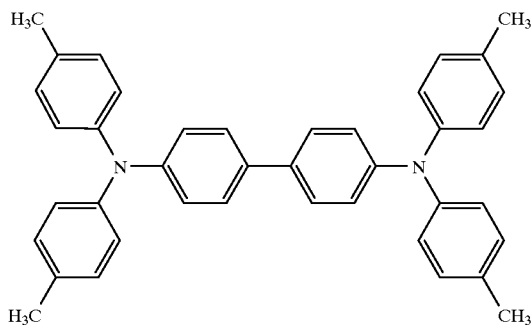
(IV-8)
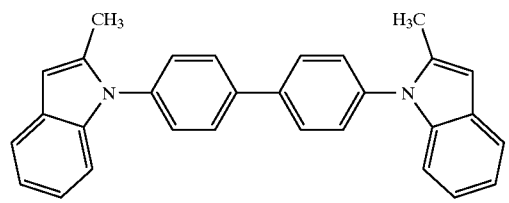
(IV-9)
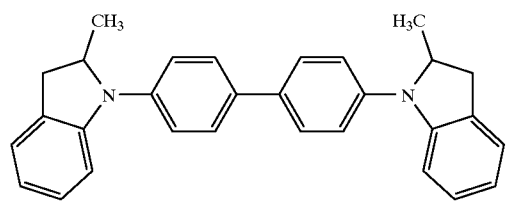
(IV-10)

-continued
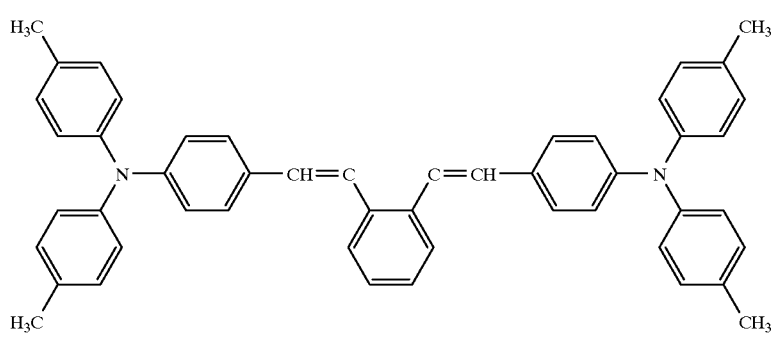
(IV-11)
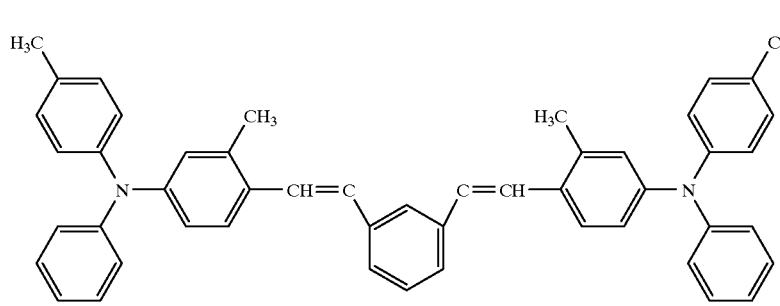
(IV-12)
The charge transport layer may also include at least one resin binder. Examples of the resin binder for the charge transport layer include various polycarbonate resins (V-1) through (V-7) described as follows:
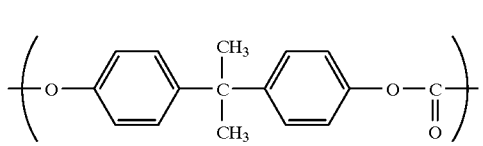
(V-1)
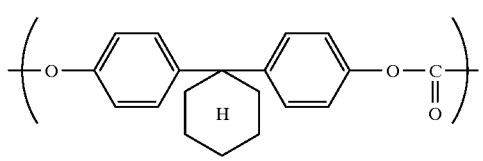
(V-2)
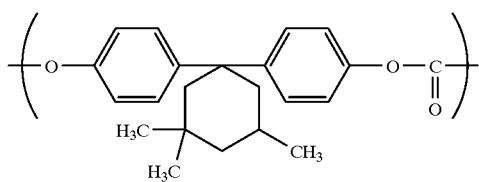
(V-3)
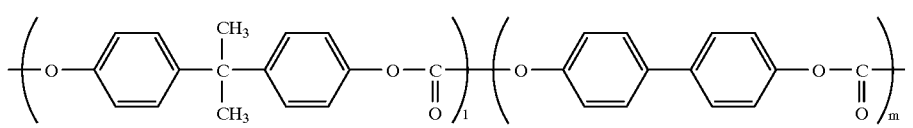
(V-4)
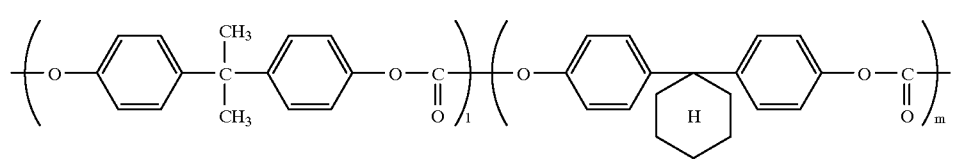
(V-5)

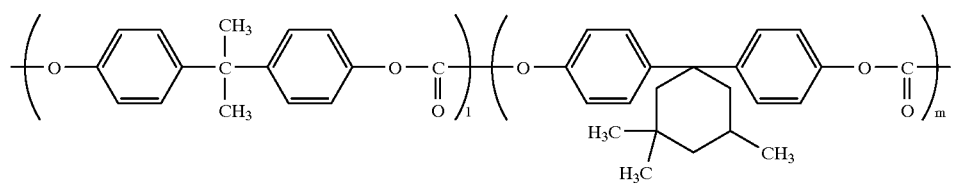
(V-6)
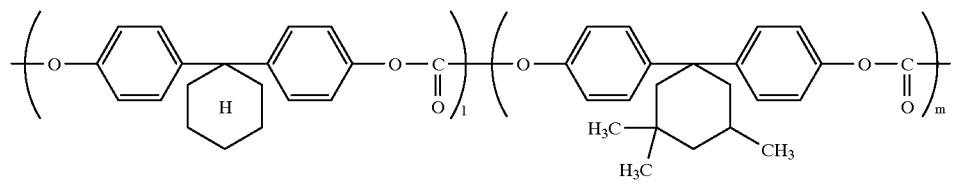
(V-7)
Amine antioxidants, phenolic antioxidants, sulfur-containing antioxidants, phosphite antioxidants, phosphor containing antioxidants and benzopinacol antioxidants (VI-1) through (VI-45) which may be used in the photoconductive film to prevent the photoconductive film from being deteriorated by ozone have the following formulas:
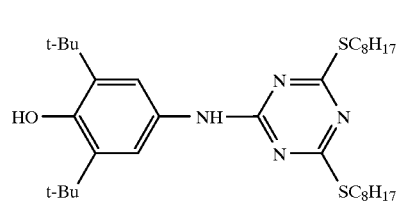
(VI-1)
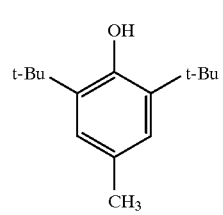
(VI-2)
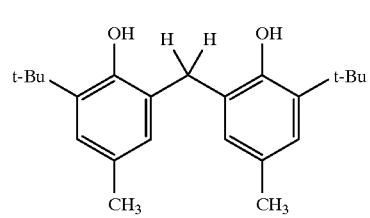
(VI-3)
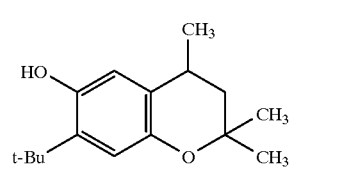
(VI-4)
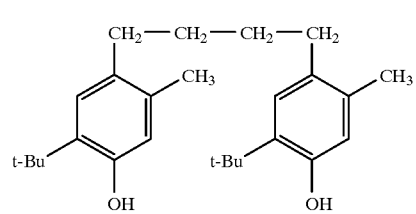
(VI-5)

-continued
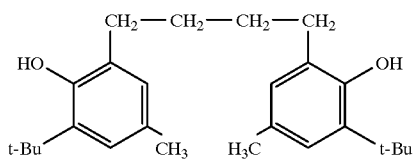
(VI-6)
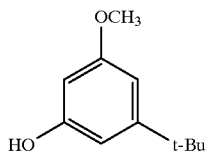
(VI-7)
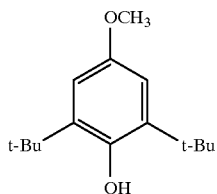
(VI-8)
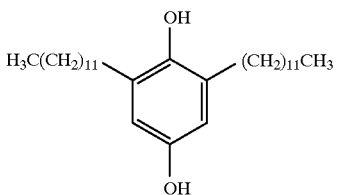
(VI-9)
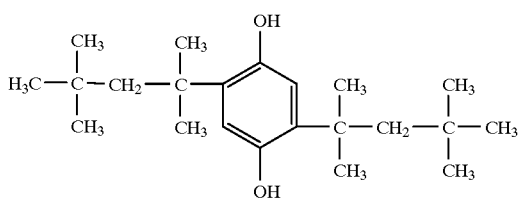
(VI-10)
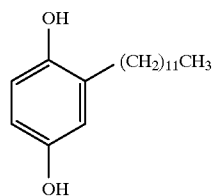
(VI-11)
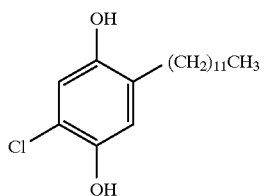
(VI-12)

-continued
(VI-13)
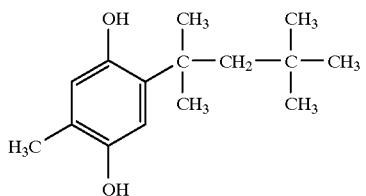
(VI-14)
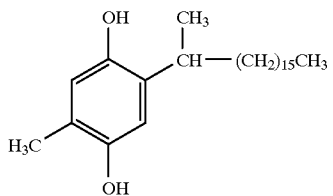
(VI-15)
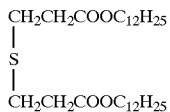
(VI-16)
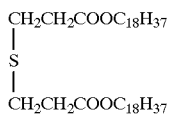
(VI-17)
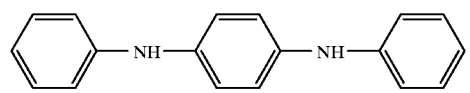
(VI-18)
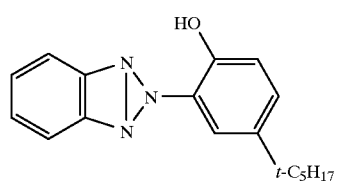
(VI-19)
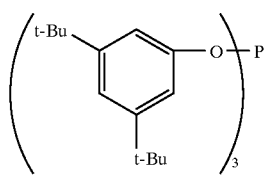
(VI-20)
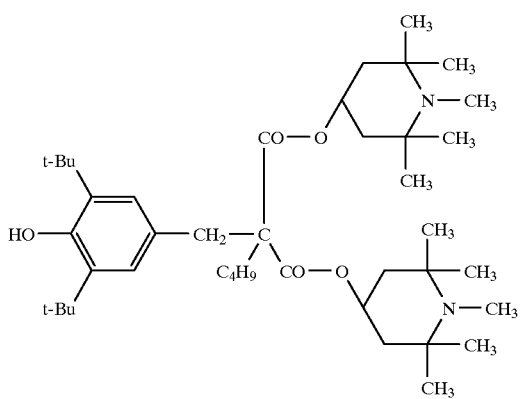

-continued
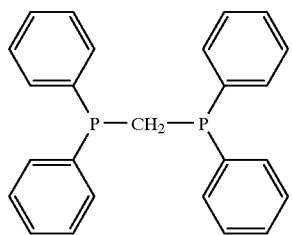
(VI-21)
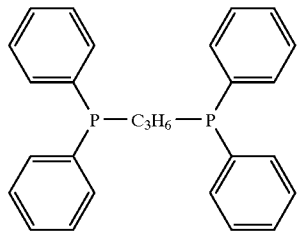
(VI-22)
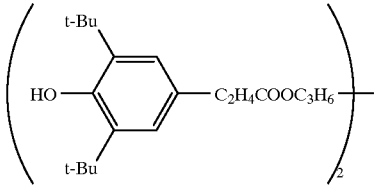
(VI-23)
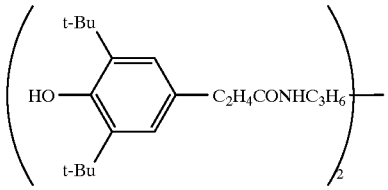
(VI-24)
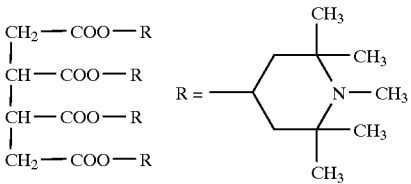
(VI-25)
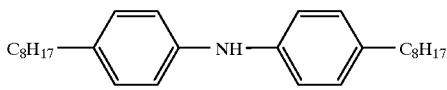
(VI-26)
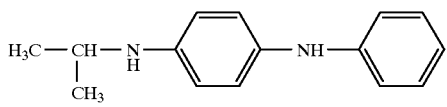
(VI-27)
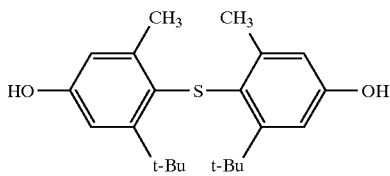
(VI-28)

-continued
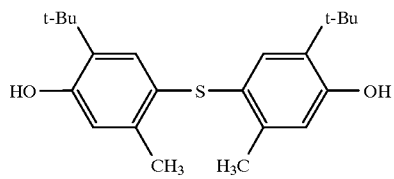
(VI-29)
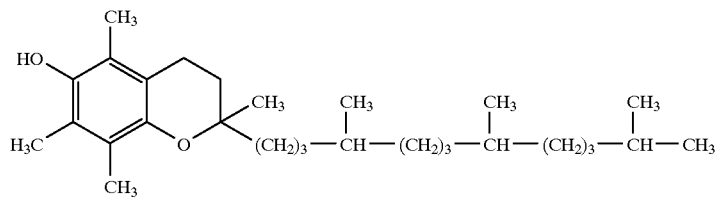
(VI-30)
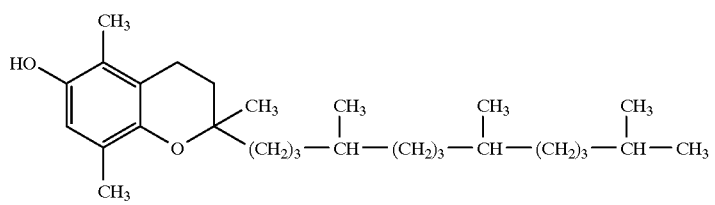
(VI-31)
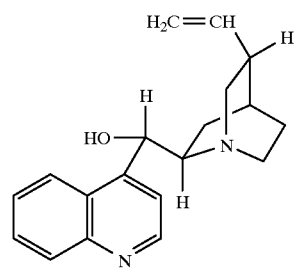
(VI-32)
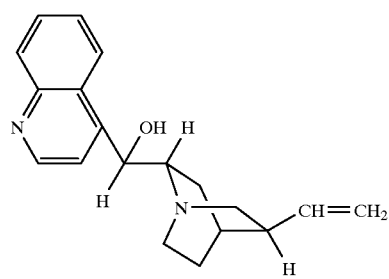
(VI-33)
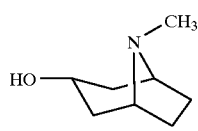
(VI-34)
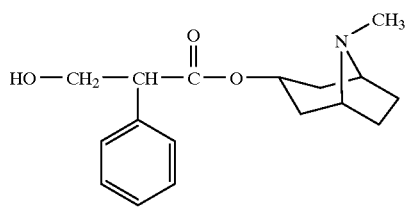
(VI-35)

-continued
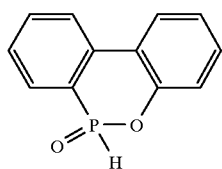
(VI-36)
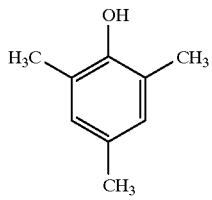
(VI-37)
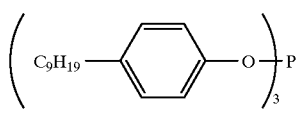
(VI-38)
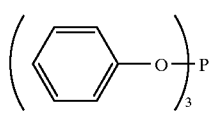
(VI-39)
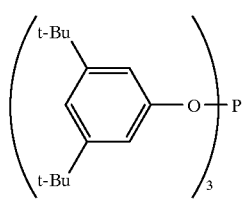
(VI-40)
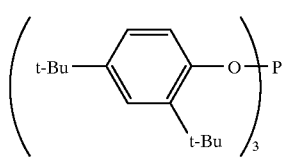
(VI-41)
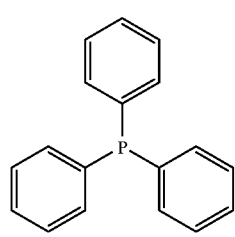
(VI-42)
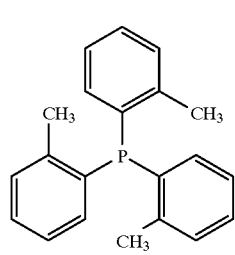
(VI-43)

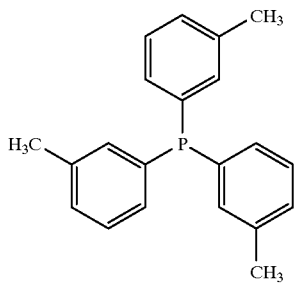

(VI-44)

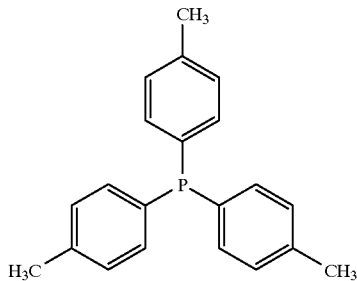

(VI-45)

This invention will be explained hereinafter with reference to the accompanied drawing figures which illustrate the photoconductive film of the invention that contains the foregoing compounds.

Figure 2:
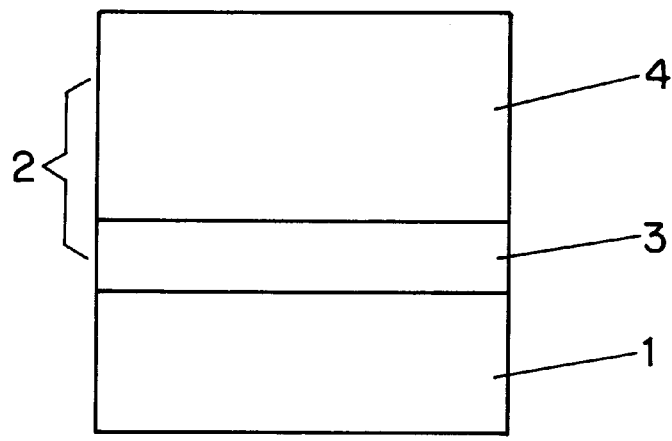
FIG. 2 shows a cross section of a negative-charging laminate-type electrophotographic photoconductor according to the present invention.
Figure 3:
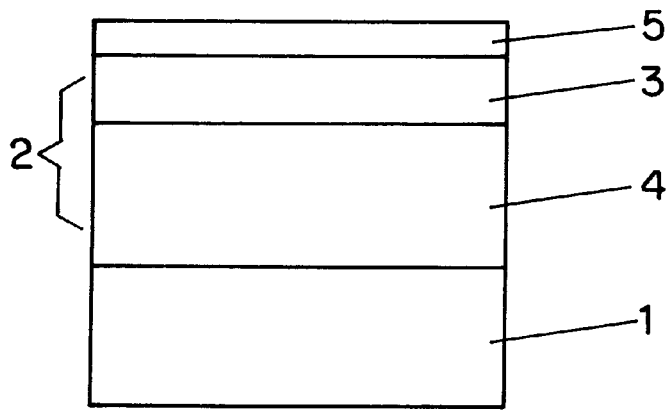
FIG. 3 shows a cross section of a positive-charging laminate-type electrophotographic photoconductor according to the present invention.

FIG. 1 is a cross section of an electrophotographic photoconductor including a monolayered photoconductive film according to the present invention. FIG. 2 is a cross section of a negative-charging laminate-type electrophotographic photoconductor according to the present invention. FIG. 3 is a cross section of a positive-charging laminate-type electrophotographic photoconductor according to the present invention. In these figures, the reference numeral 1 designates a conductive substrate, 2 a photoconductive film, 3 a charge generation layer, 4 a charge transport layer, and 5 a cover layer.

The photoconductor shown in FIG. 1 is a so-called monolayered photoconductor that includes a conductive substrate 1 and a photoconductive film 2 on the conductive substrate 1. The photoconductive film 2 includes a charge generation agent and a butadiene derivative charge transport agent dispersed into a binder resin. A cover layer 5 is formed on the photoconductive film 2, if necessary.

The photoconductor shown in FIG. 2 is a so-called laminate-type photoconductor that includes a conductive substrate 1 and a photoconductive film 2 that includes a charge generation layer 3 containing a charge generation agent and a charge transport layer 4 including a butadiene derivative charge transport agent dispersed into a binder resin.

The photoconductor shown in FIG. 3 has another laminate structure in which the order of layer lamination is reversed. In this laminate-type photoconductor, a cover layer 5 is usually formed to protect the charge generation layer 3.

The photoconductor shown in FIG. 1 is manufactured by coating the dispersion liquid, which is prepared by dispersing a charge generation agent into a solution into which a charge transport agent and a binder resin are dissolved, on a conductive substrate. If necessary, a cover layer is formed on the photoconductive film by conventional coating methods.

The photoconductor shown in FIG. 2 is manufactured as follows. The charge generation layer is formed by depositing a charge generation agent by vacuum deposition on the conductive substrate, or by coating and drying a dispersion liquid, which is prepared by dissolving a charge generation agent into a solvent or by dispersing a charge generation agent into a binder resin, on the conductive substrate. Then, the charge transport layer is formed by coating and drying a solution, into which a charge transport agent and a binder resin are dissolved, on the charge generation layer.

The photoconductor shown in FIG. 3 is manufactured as follows. The charge transport layer is formed by coating and drying a solution, into which a charge transport agent and a binder resin are dissolved, on the conductive substrate. Then, the charge generation layer is formed by depositing a charge generation agent by vacuum deposition on the charge transport layer, or by coating and drying a dispersion liquid (which is prepared by dissolving a charge generation agent into a solvent or by dispersing a charge generation agent into a binder resin), on the charge transport layer. Then, a cover layer is formed on the charge generation layer by conventional coating methods.

The conductive substrate 1 functions as an electrode of the photoconductor and sustains the layers of the photoconductor. The conductive substrate 1 may be shaped with a cylindrical tube, a plate or a film. Metals such as aluminum, stainless steel and nickel, or glass or resin (treated to exhibit electrical conduction) are used for the conductive substrate 1. Insulative polymers such as casein, poly(vinyl alcohol), nylon, polyamide, melamine and cellulose, conductive polymers such as polythiophene, polypyrrole and polyaniline or polymers that contains metal oxide powder or low molecular weight compounds used for surface decoration may additionally be used in combination with the conductive substrate.

As explained above, the charge generation layer 3 is formed by depositing a charge generation agent by vacuum deposition, or by coating and drying a dispersion liquid, which is prepared by dissolving a charge generation agent into a solvent or by dispersing a charge generation agent into a binder resin. The charge generation layer 3 generates charges in response to the irradiated light. It is preferable for the charge generation layer 3 to exhibit high charge generation efficiency and high efficiency of the generated charge injection into the charge transport layer 4. It is also preferable for the charge injection efficiency not to depend on the electric field and to be sufficiently high even in the low electric field.

Pigments and dyes such as phthalocyanine (III-1) through (III-6), azo compounds (III-7) through (III-24), their derivatives, metal phthalocyanine such as titanyl phthalocyanine, quinone compounds, indigo compounds, cyanine compounds, squarylium compounds, azulenium compounds and pyrilium compounds, selenium, and selenium compounds may be used for the charge generation agent. An appropriate charge generation agent may be selected to correspond to the wavelength range of the exposure light source used for image formation. The charge generation layer must exhibit a required charge generation performance, as is well known to those skilled in the art. The charge generation performance is determined by the light absorption coefficient and the thickness of the charge generation layer, as is well understood by those skilled in the art. The charge generation layer 3 is formed to be 5 $\mu$m or less, preferably 2 $\mu$m or less, in thickness. The concentration of the charge generation component in the charge generation layer within the range as is well known to those skilled in the art. The charge generation layer may contain a charge transport agent in addition to the charge generation agent as the main component thereof.

Binder resins which may be used in the charge generation layer include polycarbonate, polyester, polyamide, polyurethane, epoxy resin, poly(vinyl butyral), poly(vinyl acetal), phenoxy resin, silicone resin, acrylic resin, vinyl chloride resin, vinylidene chloride resin, vinyl acetate resin, formaldehyde dimethyl acetal resin, formaldehyde dimethyl acetal resin, cellulose resin, their copolymers, their halides and their cyanoethyl compounds. These binder resins may be used alone or in combination.

The charge transport layer 4 is a coating film containing at least one charge transport agent dispersed in a binder resin. The charge transport agent may be selected from one or more of compounds (IV-1) through (IV-12), in concentrations which are well known to those skilled in the art. The charge transport layer 4 functions in the dark as an insulation layer that retains the charges of the photoconductive film and transports the charges injected from the charge generation layer during light reception. The charge transport layer of the photoconductive film in this invention contains, as an electron attracting compound, the at least one furan derivative or the thiophene derivative described by the foregoing general formula (I) and (II), respectively, in combination with the charge transport agent or agents. Generally, the concentration of the furan derivative or thiophene derivatives in the charge transport layer is between 0.01 and 3 wt. %, preferably between 0.1 and 2 wt. %. The charge transport layer 4 is preferably from 10 to 40 $\mu$m in thickness. Various polycarbonate resins (V-1) through (V-7), polystyrene, polyacrylate, polyphenylene etheracryl, polyester, polymetacrylate, and their copolymers may be used as the resin binder for the charge transport layer.

Amine antioxidants, phenolic antioxidants, sulfur-containing antioxidants, phosphite antioxidants and phosphorus containing antioxidants (VI-1) through (VI-45) may be used in the photoconductive film to prevent the photoconductive film from being deteriorated by ozone.

The cover layer 5 retains in the dark the charge caused by the corona discharge and transmits the light to that the photoconductive film is sensitive. It is required for the cover layer 5 to transmit the exposure light to the photoconductive film, to receive the generated charges injected thereto and to neutralize the surface charges. Organic insulative film materials such as polyester and polyamide may be used for the cover layer 5. Inorganic materials such as glass resins and $SiO_2$, and materials such as metal and metal oxide which facilitate lowering the electrical resistance may be mixed to the organic insulative film materials. The coating materials are preferably transparent as much as possible in the wavelength region in which the charge generation agent absorbs light at its maximum. The thickness of the cover layer may be set within a range such that repeated use of the photoconductor does not cause adverse effects such as residual potential rise.

The invention will be explained more in detail by way of the examples set forth below. The photoconductors of the examples were of the negative-charging laminate-type. Cylindrical aluminum tubes of 1 mm in thickness, 310 mm in length and 60 mm in outer diameter were cleaned, dried and used for the substrates of the photoconductors of the examples.

EXAMPLE 1 (E1)

Coating liquid for the undercoating film (undercoating liquid) was prepared by dissolving 10 weight parts of alcohol-soluble polyamide copolymer (CM8000 supplied from TORAY INDUSTRIES, INC.) into a solvent mixture of 45 weight parts of methanol and 45 weight parts of methylene chloride. The undercoating film of 0.1 $\mu$m in thickness was formed on the aluminum substrate by coating the undercoating liquid on the aluminum substrate by dip-coating and by drying the coating liquid at 90° C. for 30 min.

The coating liquid for the charge generation layer (charge generation coating liquid) was prepared by dispersing 1 weight part of poly (vinyl acetal) resin (S-LEC KS-1 supplied from Sekisui Chemical Co., Ltd.) and 1 weight part of the bisazo compound (III-17) as a charge generation agent into 150 weight parts of methyl ethyl ketone in a ball mill for 48 hr. The charge generation layer of 0.2 $\mu$m in thickness was formed by dip-coating the charge generation coating liquid on the undercoating film and by drying the coating liquid at 90° C. for 30 min.

The coating liquid for the charge transport layer (charge transport coating liquid) was prepared by dissolving 50 weight parts of the hydrazone compound (IV-1), 50 weight parts of the hydrazone compound (IV-2), 100 weight parts of the bisphenol A-type-biphenyl polycarbonate copolymer (V-4) (TOUGHZET supplied from IDEMITSU KOSAN CO., LTD.), 5 weight parts of the hindered phenolic compound (VI-2) and 1 weight part of the thiophene derivative (I-1) into 700 weight parts of dichloromethane. The charge transport layer having a thickness of 20 $\mu$m was formed by dip-coating the charge transport coating liquid on the charge generation layer and by drying the coating liquid at 90° C. for 30 min. Thus, the photoconductor of this example was prepared.

EXAMPLE 2 (E2)

The photoconductor of this example was prepared in the similar manner as the photoconductor of Example 1 except that the thiophene derivative (I-5) was used in substitute for the thiophene derivative (I-1).

EXAMPLE 3 (E3)

The photoconductor of this example was prepared in the similar manner as the photoconductor of Example 1 except that the thiophene derivative (I-9) was used in substitute for the thiophene derivative (I-1).

EXAMPLE 4 (E4)

The photoconductor of this example was prepared in the similar manner as the photoconductor of Example 1 except that the furan derivative (I-13) was used in substitute for the thiophene derivative (I-1).

EXAMPLE 5 (E5)

The photoconductor of this example was prepared in the similar manner as the photoconductor of Example 1 except that the thiophene derivative (II-1) was used in substitute for the thiophene derivative (I-1).

EXAMPLE 6 (E6)

The photoconductor of this example was prepared in the similar manner as the photoconductor of Example 1 except that the thiophene derivative (II-4) was used in substitute for the thiophene derivative (I-1).

EXAMPLE 7 (E7)

The photoconductor of this example was prepared in the similar manner as the photoconductor of Example 1 except that the thiophene derivative (II-7) was used in substitute for the thiophene derivative (I-1).

EXAMPLE 8 (E8)

The photoconductor of this example was prepared in the similar manner as the photoconductor of Example 1 except that the furan derivative (II-10) was used in substitute for the thiophene derivative (I-1).

EXAMPLE 9 (E9)

The photoconductor of this example was prepared in the similar manner as the photoconductor of Example 1 except that the bisazo compound (III-7) was used in substitute for the charge generation agent of Example 1.

EXAMPLE 10 (E10)

The photoconductor of this example was prepared in the similar manner as the photoconductor of Example 1 except that the bisazo compound (III-24) was used in substitute for the charge generation agent of Example 1.

EXAMPLE 11 (E11)

The photoconductor of this example was prepared in the similar manner as the photoconductor of Example 1 except that 50 weight parts of the hydrazone compound (IV-3) and 50 weight parts of the butadiene compound (IV-4) were used in substitute for the hydrazone compounds (IV-1) and (IV-2) of Example 1.

EXAMPLE 12 (E12)

The photoconductor of this example was prepared in the similar manner as the photoconductor of Example 1 except that 50 weight parts of the diamine compound (IV-10) and 50 weight parts of the distyryl compound (IV-11) were used in substitute for the hydrazone compounds (IV-1) and (IV-2) of Example 1.

EXAMPLE 13 (E13)

The photoconductor of this example was prepared in the similar manner as the photoconductor of Example 1 except that the polycarbonate resin (V-2) was used in substitute for the resin (V-4) of the charge transport layer in Example 1.

EXAMPLE 14 (E14)

The photoconductor of this example was prepared in the similar manner as the photoconductor of Example 1 except that the polycarbonate resin (V-6) was used in substitute for the resin (V-4) of the charge transport layer in Example 1.

EXAMPLE 15 (E15)

The photoconductor of this example was prepared in the similar manner as the photoconductor of Example 1 except that the compound (VI-30) was used as an antioxidant in substitute for the antioxidant (VI-2) of Example 1.

EXAMPLE 16 (E16)

The photoconductor of this example was prepared in the similar manner as the photoconductor of Example 1 except that the compound (VI-37) was used as an antioxidant in substitute for the antioxidant (VI-2) of Example 1.

Comparative Example 1 (C1)

The photoconductor of comparative example 1 was prepared in the similar manner as the photoconductor of Example 1 except that the thiophene derivative of the Example 1 was not contained in the charge transport layer in comparative example 1.

Comparative Example 2 (C2)

The photoconductor of comparative example 2 was prepared in the similar manner as the photoconductor of Example 9 except that the thiophene derivative of Example 9 was not contained in the charge transport layer in comparative example 2.

Comparative Example 3 (C3)

The photoconductor of comparative example 3 was prepared in the similar manner as the photoconductor of Example 11 except that the thiophene derivative of Example 11 was not contained in the charge transport layer in comparative example 3.

Comparative Example 4 (C4)

The photoconductor of comparative example 4 was prepared in the similar manner as the photoconductor of Example 13 except that the thiophene derivative of Example 13 was not contained in the charge transport layer in comparative example 4.

Comparative Example 5 (C5)

The photoconductor of comparative example 5 was prepared in the similar manner as the photoconductor Example 15 except that the thiophene derivative of Example 15 was not contained in the charge transport layer in comparative example 5.

The electrophotographic properties of the photoconductors of the examples and the comparative examples were evaluated in the following way.

The surface potential when the photoconductor surface was negatively charged by corona discharge at −6.0 kV in the dark for 10 min. and surface potential after the photoconductor had been left in the dark for 5 min. from the end of the corona discharge were measured, and the retention rate VK5 of the surface potential 5 min. afterward the corona discharge was obtained. Then, the half decay exposure light quantity $E_{1/2}$ (lux.s (seconds)) was obtained by measuring a period of time (sec) until the surface potential had been halved by irradiation of the white light to the photoconductor surface at the illuminance of 2 lux.

The change of the surface potential during continuous use of the photoconductor was evaluated in an analog copying machine provided with the scorotron charging process and two-components developing mechanism. The charging mechanism, exposure mechanism and charge removal mechanism of the analog copying machine were fixed at certain outputs. Each photoconductor was subjected to a running test that prints 50000 sheets of A4-size paper at an ordinary temperature (about 20° C.) and ordinary humidity (about 60% RH) environment. White paper potential Vw and black paper potential Vb were measured at the start and end of the running test, and the potential changes ΔVw and ΔVb were obtained. Table 1 lists the results.

titanyl phthalocyanine compounds (III-1) through (III-6) exhibit similar effects as those of the photoconductors of the foregoing examples which contain the azo compound for use in the analog copying machines.

The photocoductors of this invention, which include any of the furan derivatives or thiophene derivatives in the charge transport layer, exhibit excellent stability against continuous use over a long period of time for various analog copying machines, digital copying machines, printers and facsimile devices which employ the corotron method, whether employing the charging brush, the charging roller or the single-component development method. This is similar to the photoconductors of the foregoing examples which employ the scorotron method and two-component development method.

By containing at least one of the furan derivatives or thiophene derivatives described by the general formulas (I)

TABLE 1

| Specimen | Furan or thiophene | Charge generation agent | Charge transport agents | | Binder resin | Antioxidant | VK5 (%) | E½ (lux · s) | Initial | | Change | |
|---|---|---|---|---|---|---|---|---|---|---|---|---|
| | | | | | | | | | Vw (V) | Vb (V) | ΔVw (V) | ΔVb (V) |
| E 1 | I-1 | III-17 | IV-1 | IV-2 | V-4 | VI-2 | 97.0 | 0.90 | −47 | −605 | 5 | −2 |
| E 2 | I-5 | III-17 | IV-1 | IV-2 | V-4 | VI-2 | 98.5 | 0.92 | −45 | −603 | 4 | −1 |
| E 3 | I-9 | III-17 | IV-1 | IV-2 | V-4 | VI-2 | 96.4 | 1.02 | −45 | −605 | 0 | −3 |
| E 4 | I-13 | III-17 | IV-1 | IV-2 | V-4 | VI-2 | 95.5 | 0.88 | −44 | −603 | 5 | 0 |
| E 5 | II-1 | III-17 | IV-1 | IV-2 | V-4 | VI-2 | 96.7 | 0.93 | −48 | −604 | 7 | −2 |
| E 6 | II-4 | III-17 | IV-1 | IV-2 | V-4 | VI-2 | 98.0 | 0.95 | −47 | −605 | 4 | −3 |
| E 7 | II-7 | III-17 | IV-1 | IV-2 | V-4 | VI-2 | 97.0 | 0.90 | −45 | −607 | 3 | −3 |
| E 8 | II-10 | III-17 | IV-1 | IV-2 | V-4 | VI-2 | 96.2 | 0.97 | −45 | −605 | 0 | −5 |
| E 9 | I-1 | III-7 | IV-1 | IV-2 | V-4 | VI-2 | 95.8 | 1.06 | −45 | −607 | 5 | −3 |
| E 10 | I-1 | III-24 | IV-1 | IV-2 | V-4 | VI-2 | 96.7 | 1.03 | −45 | −605 | 2 | −4 |
| E 11 | I-1 | III-17 | IV-3 | IV-4 | V-4 | VI-2 | 97.2 | 0.92 | −45 | −605 | 3 | −4 |
| E 12 | I-1 | III-17 | IV-10 | IV-11 | V-4 | VI-2 | 98.0 | 1.03 | −45 | −607 | 5 | 0 |
| E 13 | I-1 | III-17 | IV-1 | IV-2 | V-2 | VI-2 | 98.0 | 0.99 | −45 | −605 | 6 | −3 |
| E 14 | I-1 | III-17 | IV-1 | IV-2 | V-6 | VI-2 | 98.0 | 0.95 | −45 | −607 | 2 | −5 |
| E 15 | I-1 | III-17 | IV-1 | IV-2 | V-4 | VI-30 | 98.0 | 1.05 | −45 | −605 | 0 | −1 |
| E 16 | I-1 | III-17 | IV-1 | IV-2 | V-4 | VI-37 | 98.0 | 0.99 | −45 | −605 | 2 | −2 |
| C 1 | — | III-17 | IV-1 | IV-2 | V-4 | VI-2 | 96.0 | 0.99 | −45 | −610 | 82 | −26 |
| C 2 | — | III-7 | IV-1 | IV-2 | V-4 | VI-2 | 97.0 | 0.95 | −46 | −608 | 55 | −19 |
| C 3 | — | III-17 | IV-3 | IV-4 | V-4 | VI-2 | 95.5 | 1.03 | −45 | −605 | 59 | −28 |
| C 4 | — | III-17 | IV-1 | IV-2 | V-2 | VI-2 | 97.4 | 1.03 | −44 | −609 | 76 | −16 |
| C 5 | — | III-17 | IV-1 | IV-2 | V-4 | VI-30 | 95.2 | 1.01 | −45 | −605 | 93 | −18 |

As Table 1 clearly indicates, the comparative photoconductors which do not contain any furan derivative or thiophene derivative in the charge transport layer thereof cause much larger potential changes as compared with the photoconductors of the invention. That is, the comparative photoconductors do not exhibit excellent electrophotographic properties. Comparing the photoconductors of Examples E1, E9 and E10, it has been demonstrated that stable electrophotographic properties were obtained from the photoconductors of this invention using different charge generation agents. Since the favorable effects of the furan derivatives or thiophene derivatives were obtained by Examples E11 and E12 (which include different charge transport agents), by Examples E13 and E14 (which include different resin binders for the charge transport layer), and by Examples E15 and E16 (which include different antioxidants), the furan derivatives and the thiophene derivatives of the invention have been shown as advantageous for various electrophotographic photoconductors.

By containing the furan derivatives or thiophene derivatives in the charge transport layer, the photoconductors for printers, digital copying machines or facsimile devices which contain any of the metal free phthalocyanine and or (II) in the photoconductive film according to this invention, a highly sensitive electrophotographic photoconductor that is stable enough to endure repeated continuous use for a long time in practical electrophotographic processes is obtained.

From the foregoing, it is readily apparent that new and useful electrophotographic photoconductors have been described and illustrated which fulfill all of the aforestated objectives. It is of course understood that such modifications, alterations and adaptations as will readily occur to those skilled in the art are intended within the scope of the invention.

What is claimed is:

1. An electrophotographic photoconductor comprising:

(a) a conductive substrate; and (b) a photoconductive film on said conductive substrate, said photoconductive film comprising at least one charge generation agent, at least one charge transport agent, and at least one furan derivative or thiophene derivative, said furan or thiophene derivative having the general formula:

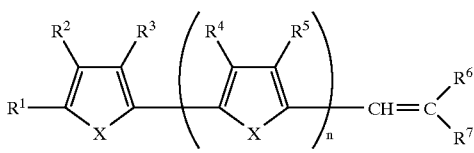 (I)

wherein
- $R^1$ is a hydrogen atom, halogen atom, substituted or non-substituted alkyl group, alkoxy group, cyano group, substituted or non-substituted heterocyclic group, or substituted or non-substituted aromatic group,
- $R^2$ is a hydrogen atom, halogen atom, substituted or non-substituted alkyl group, alkoxy group, cyano group, substituted or non-substituted heterocyclic group, or substituted or non-substituted aromatic group,
- $R^3$ is a hydrogen atom, halogen atom, substituted or non-substituted alkyl group, alkoxy group, cyano group, substituted or non-substituted heterocyclic group, or substituted or non-substituted aromatic group,
- $R^4$ is a hydrogen atom, halogen atom, substituted or non-substituted alkyl group, alkoxy group, cyano group, substituted or non-substituted heterocyclic group, or substituted or non-substituted aromatic group,
- $R^5$ is a hydrogen atom, halogen atom, substituted or non-substituted alkyl group, alkoxy group, cyano group, substituted or non-substituted heterocyclic group, or substituted or non-substituted aromatic group,
- $R^6$ is a cyano group, or alkoxycarbonyl group,
- $R^7$ is a cyano group, or alkoxycarbonyl group,
- X is an oxygen atom or sulfur atom, and
- n is an integer of 0 or 1, or

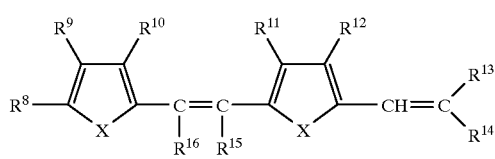 (II)

wherein
- $R^8$ is a hydrogen atom, halogen atom, substituted or non-substituted alkyl group, alkoxy group, cyano group, substituted or non-substituted heterocyclic group, or substituted or non-substituted aromatic group,
- $R^9$ is a hydrogen atom, halogen atom, substituted or non-substituted alkyl group, alkoxy group, cyano group, substituted or non-substituted heterocyclic group, or substituted or non-substituted aromatic group,
- $R^{10}$ is a hydrogen atom, halogen atom, substituted or non-substituted alkyl group, alkoxy group, cyano group, substituted or non-substituted heterocyclic group, or substituted or non-substituted aromatic group,
- $R^{11}$ is a hydrogen atom, halogen atom, substituted or non-substituted alkyl group, alkoxy group, cyano group, substituted or non-substituted heterocyclic group, or substituted or non-substituted aromatic group,
- $R^{12}$ is a hydrogen atom, halogen atom, substituted or non-substituted alkyl group, alkoxy group, cyano group, substituted or non-substituted heterocyclic group, or substituted or non-substituted aromatic group,
- $R^{15}$ is a hydrogen atom, halogen atom, substituted or non-substituted alkyl group, alkoxy group, cyano group, substituted or non-substituted heterocyclic group, or substituted or non-substituted aromatic group,
- $R^{16}$ is a hydrogen atom, halogen atom, substituted or non-substituted alkyl group, alkoxy group, cyano group, substituted or non-substituted heterocyclic group, or substituted or non-substituted aromatic group,
- $R^{13}$ is a cyano group, or alkoxycarbonyl group,
- $R^{14}$ is a cyano group, or alkoxycarbonyl group, and
- X is an oxygen atom or sulfur atom.

2. The electrophotographic photoconductor of claim 1, in which the furan or thiophene derivative is of general formula (I).

3. The electrophotographic photoconductor of claim 1, in which the furan or thiophene derivative is of general formula (II).

4. The electrophotographic photoconductor according to claim 2, wherein the furan or thiophene derivative is selected from the group consisting of one or more furan derivatives and thiophene derivatives of formula (I) having the following specific formulas:

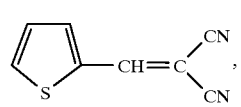 I-1

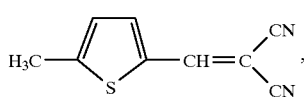 I-2

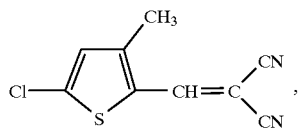 I-3

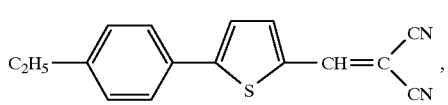 I-4

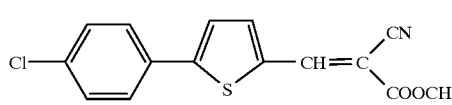 I-5

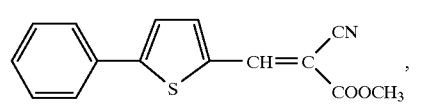 I-6

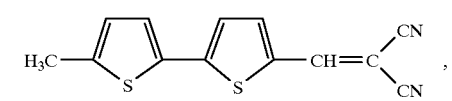
I-7

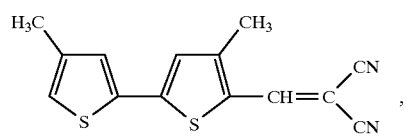
I-8

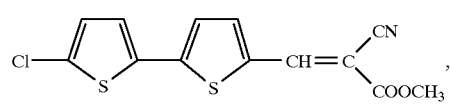
I-9

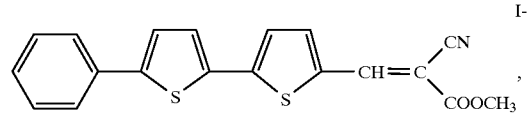
I-10

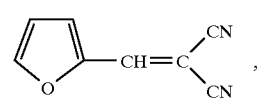
I-11

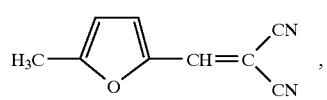
I-12

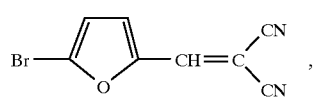
I-13

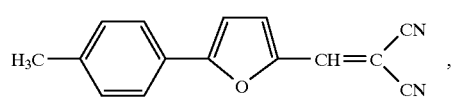
I-14

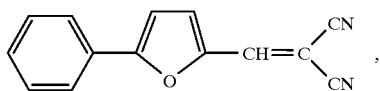
I-15

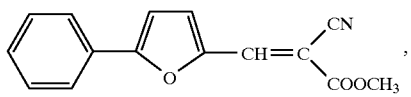
I-16

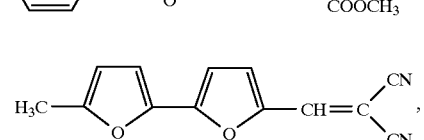
I-17

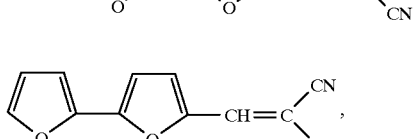
I-18

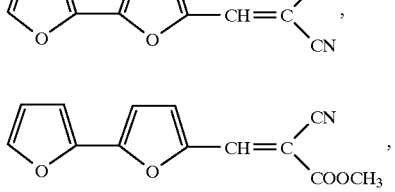
I-19

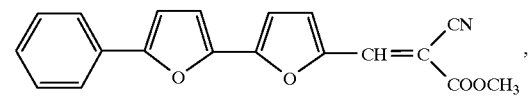
I-20

5. The electrophotographic photoconductor according to claim 1, wherein said charge transport layer has a thickness between 10 and 40 μm.

6. An electrophotographic photoconductor according to claim 3, wherein the furan or thiophene derivative is selected from the group consisting of one or more furan derivatives and thiophene derivatives of formula (II) having the following specific formulas:

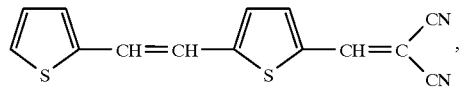
II-1

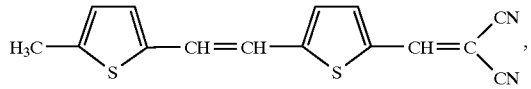
II-2

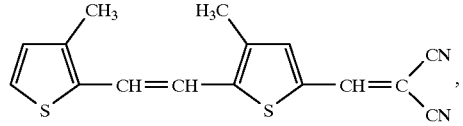
II-3

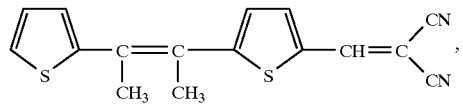
II-4

II-5
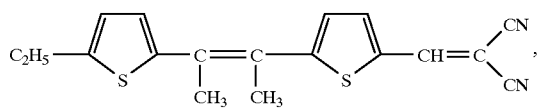
II-6
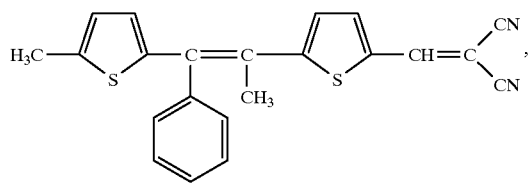
II-7
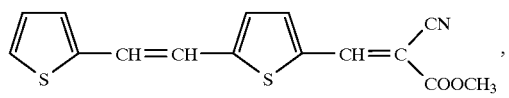
II-8
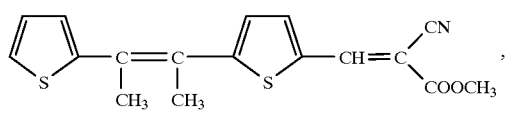
II-9
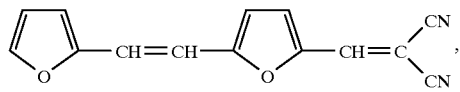
II-10
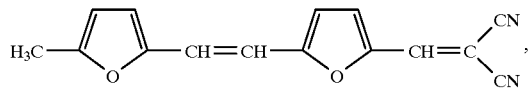
II-11
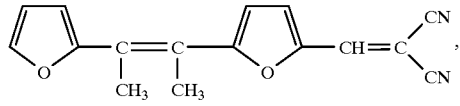
II-12
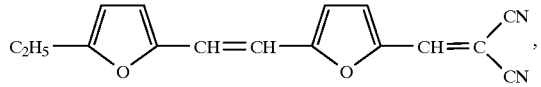
II-13
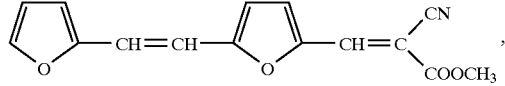
II-14
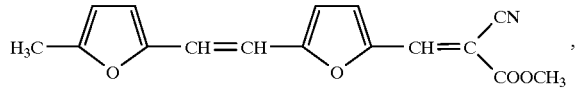
II-15
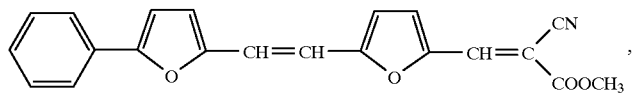

and 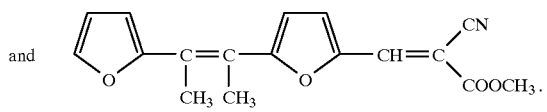 II-16

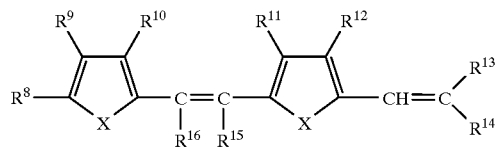

7. An electrophotographic photoconductor comprising:
(a) a conductive substrate; and
(b) a photoconductive film on said conductive substrate, said photoconductive film comprising at least one charge generation agent, at least one charge transport agent, and at least one furan derivative or thiophene derivative, said furan or thiophene derivative having the general formula:

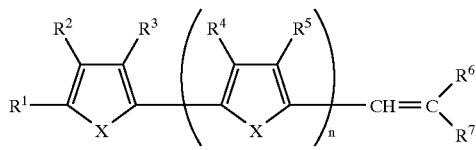 (I)

wherein
- $R^1$ is a hydrogen atom, halogen atom, substituted or non-substituted alkyl group, alkoxy group, cyano group, substituted or non-substituted heterocyclic group, or substituted or non-substituted aromatic group,
- $R^2$ is a hydrogen atom, halogen atom, substituted or non-substituted alkyl group, alkoxy group, cyano group, substituted or non-substituted heterocyclic group, or substituted or non-substituted aromatic group,
- $R^3$ is a hydrogen atom, halogen atom, substituted or non-substituted alkyl group, alkoxy group, cyano group, substituted or non-substituted heterocyclic group, or substituted or non-substituted aromatic group,
- $R^4$ is a hydrogen atom, halogen atom, substituted or non-substituted alkyl group, alkoxy group, cyano group, substituted or non-substituted heterocyclic group, or substituted or non-substituted aromatic group,
- $R^5$ is a hydrogen atom, halogen atom, substituted or non-substituted alkyl group, alkoxy group, cyano group, substituted or non-substituted heterocyclic group, or substituted or non-substituted aromatic group,
- $R^6$ is a cyano group, or alkoxycarbonyl group,
- $R^7$ is a cyano group, or alkoxycarbonyl group,
- X is an oxygen atom or sulfur atom, and
- n is an integer of 0 or 1.

8. An electrophotographic photoconductor comprising:
(a) a conductive substrate; and
(b) a photoconductive film on said conductive substrate, said photoconductive film comprising at least one charge generation agent, at least one charge transport agent, and at least one furan derivative or thiophene derivative, said furan or thiophene derivative having the general formula:

(II)

wherein
- $R^8$ is a hydrogen atom, halogen atom, substituted or non-substituted alkyl group, alkoxy group, cyano group, substituted or non-substituted heterocyclic group, or substituted or non-substituted aromatic group,
- $R^9$ is a hydrogen atom, halogen atom, substituted or non-substituted alkyl group, alkoxy group, cyano group, substituted or non-substituted heterocyclic group, or substituted or non-substituted aromatic group,
- $R^{10}$ is a hydrogen atom, halogen atom, substituted or non-substituted alkyl group, alkoxy group, cyano group, substituted or non-substituted heterocyclic group, or substituted or non-substituted aromatic group,
- $R^{11}$ is a hydrogen atom, halogen atom, substituted or non-substituted alkyl group, alkoxy group, cyano group, substituted or non-substituted heterocyclic group, or substituted or non-substituted aromatic group,
- $R^{12}$ is a hydrogen atom, halogen atom, substituted or non-substituted alkyl group, alkoxy group, cyano group, substituted or non-substituted heterocyclic group, or substituted or non-substituted aromatic group,
- $R^{15}$ is a hydrogen atom, halogen atom, substituted or non-substituted alkyl group, alkoxy group, cyano group, substituted or non-substituted heterocyclic group, or substituted or non-substituted aromatic group,
- $R^{16}$ is a hydrogen atom, halogen atom, substituted or non-substituted alkyl group, alkoxy group, cyano group, substituted or non-substituted heterocyclic group, or substituted or non-substituted aromatic group,
- $R^{13}$ is a cyano group, or alkoxycarbonyl group,
- $R^{14}$ is a cyano group, or alkoxycarbonyl group, and
- X is an oxygen atom or sulfur atom.

* * * * *